United States Patent [19]

Hill

[11] Patent Number: 4,559,936
[45] Date of Patent: Dec. 24, 1985

[54] BONE PLUGGING APPARATUS

[76] Inventor: Edward B. Hill, 700 Luzerne St., Johnstown, Pa. 15905

[21] Appl. No.: 536,972

[22] Filed: Sep. 29, 1983

[51] Int. Cl.$^4$ .............................................. A61F 5/04
[52] U.S. Cl. ............................ 128/92 R; 128/92 EA; 128/310
[58] Field of Search ........... 128/92 E, 92 EB, 92 EC, 128/92 R, 305.1, 310, 92 H, 92 EA

[56] References Cited

U.S. PATENT DOCUMENTS

| | | |
|---|---|---|
| 1,123,730 | 1/1915 | Greenfield . |
| 1,476,611 | 12/1923 | Hines . |
| 1,742,224 | 1/1930 | Swartz . |
| 2,919,692 | 1/1960 | Ackermann . |
| 3,850,158 | 11/1974 | Elias et al. . |
| 3,949,747 | 4/1976 | Hevesy ................................ 128/310 |
| 4,005,945 | 2/1977 | Gutman . |
| 4,059,115 | 11/1977 | Jumashev et al. ................... 128/310 |
| 4,293,962 | 10/1981 | Fuson . |
| 4,337,773 | 7/1982 | Raftopoulos et al. . |
| 4,416,278 | 11/1983 | Miller ................................. 128/92 E |

FOREIGN PATENT DOCUMENTS 625699 9/1978 U.S.S.R. .

OTHER PUBLICATIONS

Dow Corning Wright, Arlington, TN 38002, "Titan TM Total Hip System", brochure L095–0103, 1983.
Zimmer, Warsaw, IN 46580, pp. A217–A219, 1981 catalog.

Primary Examiner—Gene Mancene
Assistant Examiner—C. W. Shedd
Attorney, Agent, or Firm—Cushman, Darby & Cushman

[57] ABSTRACT

A method and apparatus for practicing hip arthroplasty facilitate the quick and effective positioning of a bone plug of desired size into a femoral medullary canal at a desired depth so that the bone plug acts as a dam for methylmethacrylate cement which holds the prosthesis in place in the femoral medullary canal. One or more elongated rods have enlarged disc-shaped ends of different diameters, with color coding at the ends corresponding to the diameters, are provided. The rods have distance calibrating indicia along the length thereof. A cutting tool having an internal bone-plugging diameter corresponding to the diameter of each of the rod ends is provided, with common color coding on the cutting tool and the corresponding rod end. A common support mounts a resected femoral head holding device (which also guides the cutting tool), and the rods and cutting tools in storage positions, and also can support the rods in positions for use in removing bone plugs from the cutting tools.

19 Claims, 14 Drawing Figures

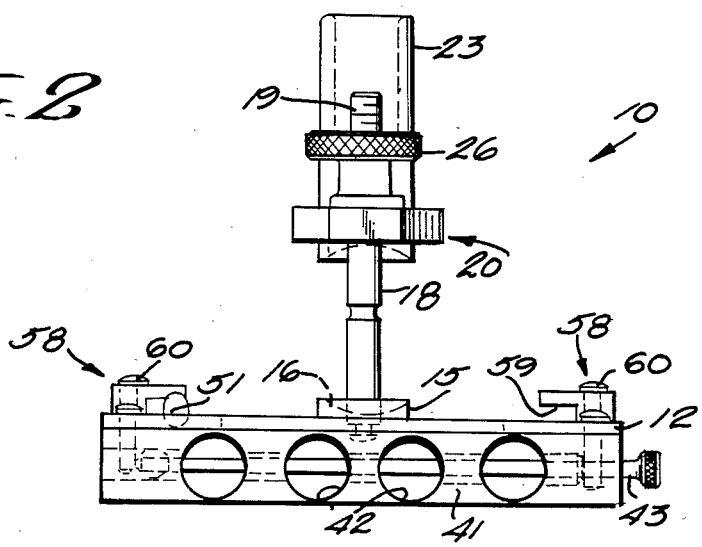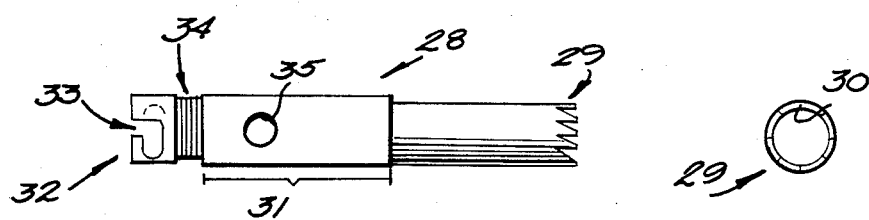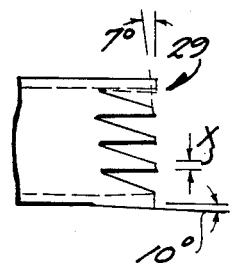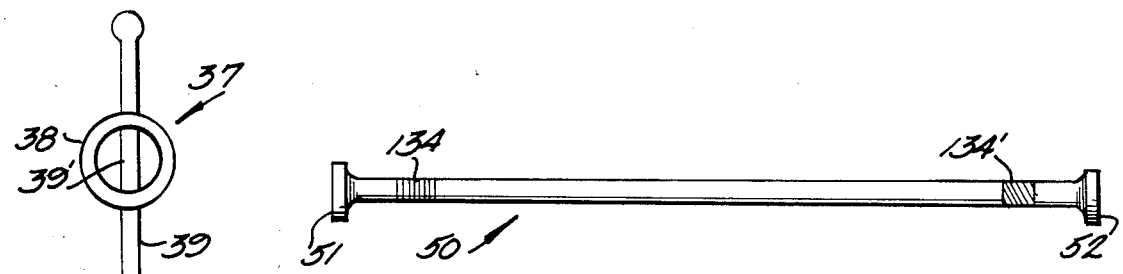

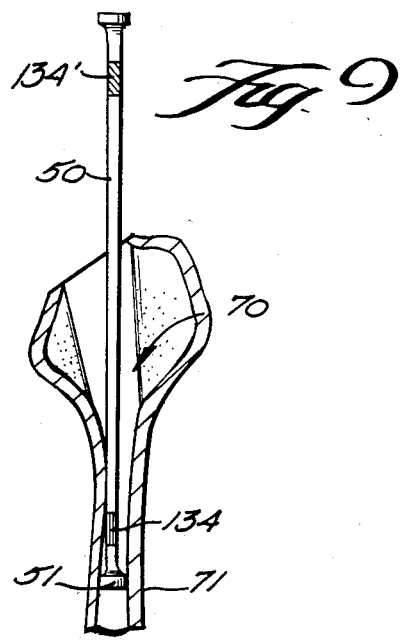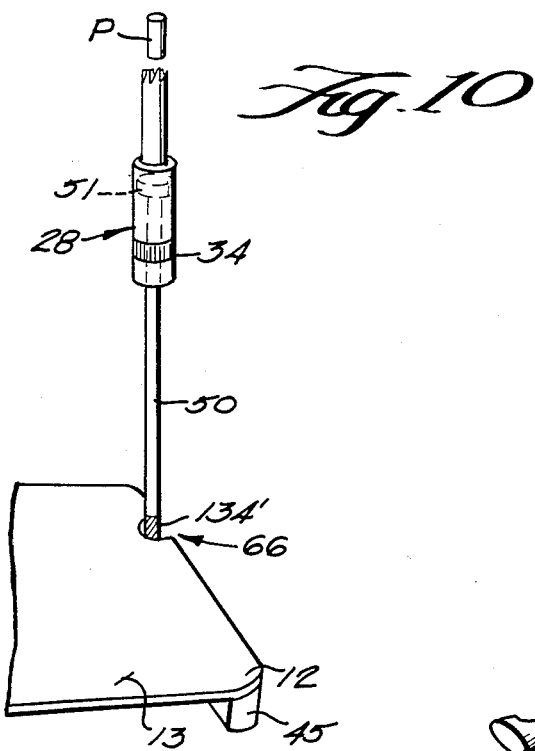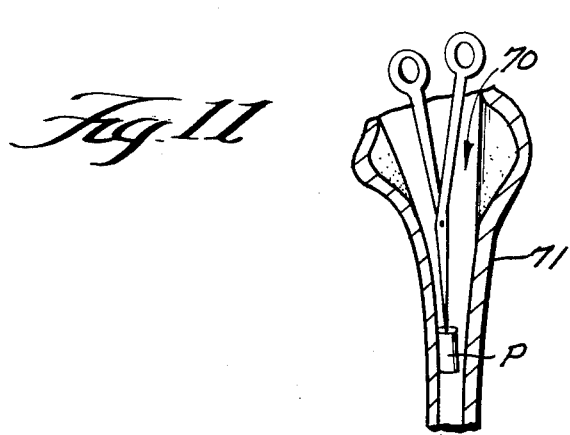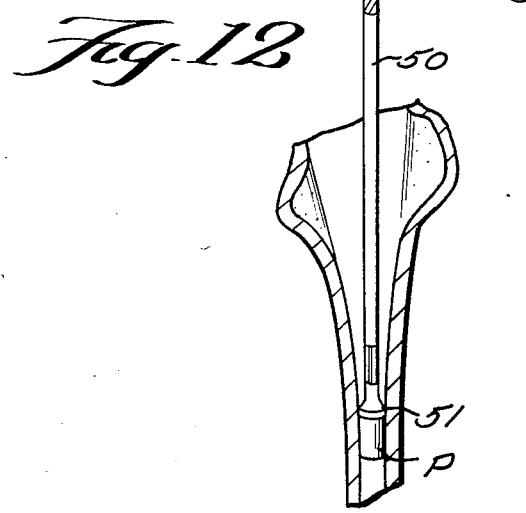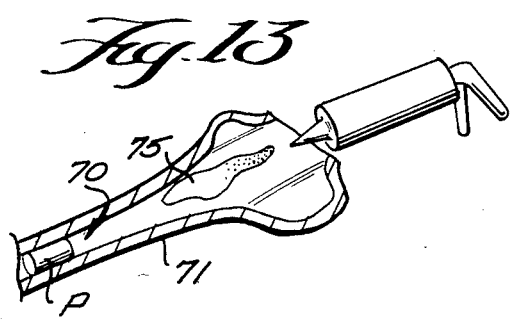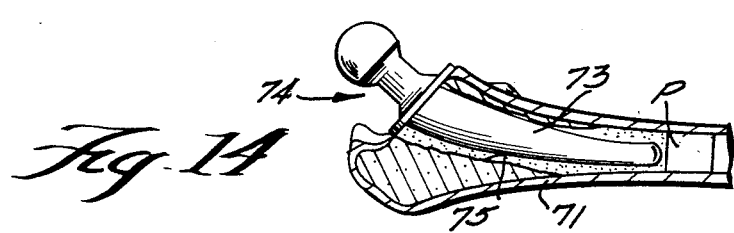

BONE PLUGGING APPARATUS

BACKGROUND AND SUMMARY OF THE INVENTION

In conventional hip arthroplasty, it is desirable to form a bone plug from the resected (severed) femoral head, and use that bone plug as a dam for the cement inserted into the femur medullary canal to hold the prosthesis in place. The cutting of the bone plug of the desired size depending upon the particular femoral medullary canal into which it is to be inserted, and the positioning of the bone plug at the proper depth, conventionally require relatively complicated procedures and equipment, and are relatively time consuming. According to the present invention a method of performing hip arthroplasty, and apparatus facilitating practice of the method, are provided which simplify the procedures with respect to desired formation and placement of the bone plug, and reduce the time consumed.

According to one aspect of the present invention, an apparatus is provided for facilitating hip arthroplasty or the like. That apparatus includes: A rod having first and second enlarged generally disc-shaped ends, each end disc having a predetermined diameter, the first end disc diameter being different than the second end disc diameter. Linear calibrating indicia formed on the rod at predetermined distances from each of the ends thereof. Correlating indicia associated with each of the ends of the rod, the indicia for the first end distinct from that for the second end. First and second hollow bone cutting tools of different effective internal diameter, the first tool having an internal diameter substantially identical to the diameter of the rod first end disc diameter, and the first tool having correlating indicia corresponding to that for the rod first end and the second tool having an effective internal diameter substantially identical to the diameter of the rod second end disc diameter, and having correlating indicia corresponding to that for the rod second end.

The correlating indicia preferably comprise colors, and preferably a plurality of rods, and twice the number of cutting tools as rods, are provided, so that the bone plug may be of the desired size. Also, a holding device for holding the resected femoral head, and for guiding the cutting tool, is provided mounted on a support, and the support is dimensioned so that it also holds the rods and tools in storage positions. A notch formed in the support is provided to hold the rod in an upright position when the rod is utilized for removing a bone plug from a cutting tool.

According to another aspect of the present invention there is provided: A support stationarily mounting a cup for receipt of a bone portion, and having a pair of rods upstanding from, and straddling, the cup. A movable holding component including means defining openings therein for receipt of the rods so that the movable component is movable toward and away from the cup guided by the rods. Affixing means for affixing the movable component to the rods at a predetermined position to thereby clamp a bone portion between the cup and the movable component. A tubular guide disposed in operative association with the movable holding component, and having an interior diameter aligned with the cup when the movable component is held in operative association with respect to the cup, receiving said rods. A plurality of differently dimensioned bone cutting tools, each bone cutting tool having an external diameter guide portion corresponding to the internal diameter of said tubular guide, and each cutting tool having a different internal diameter, corresponding to the diameter of a bone plug to be formed thereby. And, wherein the support includes surface means for mounting each of the tools in a storage position.

The rods utilized in the practice of the present invention are per se distinct from other hand tools in the art, having as they do enlarged disc-shaped ends of different diameters, distance calibrations from both ends extending along the length thereof, and color coding of the ends.

The invention further comprises a method of practicing hip arthroplasty. The method includes the following steps: (a) Severing the femur head from the femur of the hip undergoing arthroplasty. (b) Calibrating the internal diameter of the femur hollow medullary canal by inserting rod ends until a rod end is found having a disc diameter that fits snugly, but does not bind, within the medullary canal at the isthmus. (c) Simultaneously with step (b), when inserting the rod having the desired disc end diameter, determining the depth from the level of the femoral neck transection including by reading length calibrating indicia on the rod. (d) Selecting the cutting tool having correlating indicia corresponding to the correlating indicia of the selected rod disc end. (e) Utilizing the selected cutting tool, forming a bone plug from the resected femoral head. (f) Cutting the bone plug, if necessary, to the desired length. (g) Inserting the bone plug into the femoral medullary canal. (h) Utilizing the selected rod, with the selected rod end in contact with the bone plug, impacting the rod to drive the bone plug to the desired depth, as determined by reading the length calibrating indicia on the rod. (i) Inserting a suitable cement into the femoral medullary canal. (j) Disposing a prosthesis in operative association with the femoral medullary canal so that the prosthesis is held in the appropriate position by the cement; and (k) between steps (e) and (f), removing the bone plug from the cutting tool by forcing the selected rod disc end into the hollow cutting tool to contact the bone plug and move it out of the cutting tool.

It is the primary object of the present invention to provide a method for practicing hip arthroplasty, and apparatus suitable for use in the practice of hip arthroplasty, that minimize the difficulties and time associated with obtaining and positioning a desired bone plug in the femoral medullary canal. This and other objects of the invention will become clear from an inspection of the detailed description of the invention, and from the appended claims.

BRIEF DESCRIPTION OF THE DRAWINGS

FIG. 2 is an end view, looking in the direction of arrow A in FIG. 1, of the apparatus of FIG. 1;

FIG. 4 is a side detail view of an exemplary cutting tool according to the present invention;

FIG. 5 is an end view of the tool of FIG. 4, looking in at the operative cutting end thereof;

FIG. 6 is a detail view of the cutting end of the tool of FIG. 4;

FIG. 7 is a top plan view of a handle that may be utilized to effect rotation of the cutting tool of FIG. 4;

FIG. 8 is a side view of an exemplary calibrating rod according to the present invention; and FIGS. 9 through 14 are schematic illustrations showing the use of the apparatus of FIGS. 1 through 8 for the practice of a method of hip arthroplasty according to the present invention.

DETAILED DESCRIPTION OF THE DRAWINGS

Figure 1:
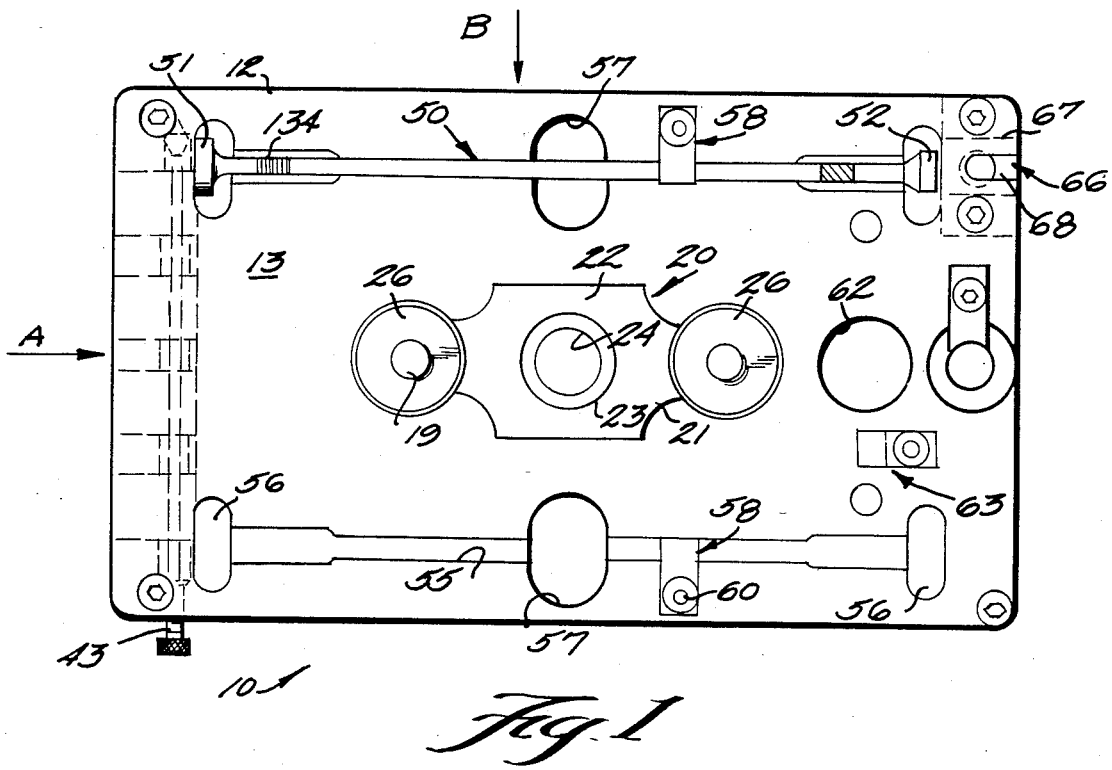
FIG. 1 is a top plan view of exemplary apparatus according to the present invention, and showing an elongated calibrating rod mounted in a storage position.
Figure 3:
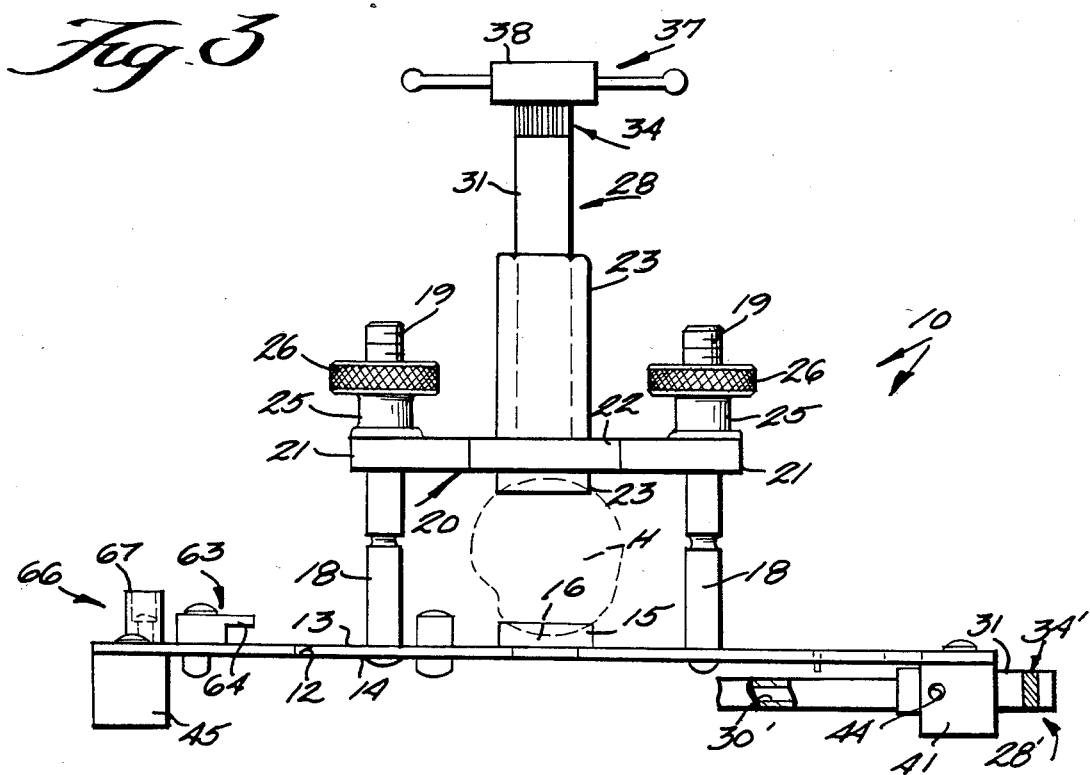
FIG. 3 is a side view, as viewed in the direction of arrow B in FIG. 1, of the apparatus of FIG. 1, and showing one cutting tool in storage position and another in operative association with the cutting tool guide, for forming a bone plug from a resected femoral head (shown in dotted line)

The structure illustrated generally by reference numeral 10 in FIGS. 1 through 3 comprises a structure for supporting calibrating rods, cutting tools, and other components according to the invention—and utilized in the practice of the method according to the invention—in storage position, as well as operative position for cutting a bone plug of predetermined size, and removing the bone plug from the cutting tool. The device 10 primarily comprises a support including a support plate 12 having a top surface 13 and a bottom surface 14. Upstanding from the top surface 13 is a cup 15, having a radiused depression (shown in dotted line and referenced by numeral 16) for receipt of a bone portion, such as the femoral head H (see FIG. 3), and a pair of studs 18 upstanding from surface 13 and generally perpendicular thereto, each stud preferably including a threaded end portion 19, and the studs straddling the cup 15.

For cooperation with the cup 15 and rods 18 for holding a resected femoral head H in place, there is provided a movable holding component shown generally by reference numeral 20. The component 20 includes a pair of ears 21, each including means defining an opening (not shown) for receipt of the stud 18 therein and through which the stud passes during use. The component 20 also includes a center section 22 including a tubular guide 23, the interior passageway 24 (see FIG. 1) of the guide 23 disposed in-line with the cup 15. Interiorly threaded nuts 25, with knob portions 26, are disposed in threaded engagement with the threaded ends 19 of the studs 18, and apply a force to the ears 21 forcing the holding component 20 into contact with the resected femoral head H to thereby clamp it between the guide tube 23 and the cup 15.

A plurality of hollow cutting tools of different effective internal diameter are provided for cooperation with the guide 23, and the like, for forming a bone plug of desired diameter from the resected femoral head H. Two such cutting tools, 28, 28', are shown in operative, and storage, positions with respect to the support plate 12 in FIG. 3, and FIGS. 4 through 5 show details of the construction of the cutting tools.

The cutting tool 28 (see FIGS. 3 and 4) includes a cutting end portion 29, having serrations preferably having the particular construction and angular relationship as illustrated in FIGS. 4 and 6. Such a cutting configuration is known per se. The cutting tool 28 is hollow having a predetermined internal diameter 30. The tool 28 further includes a portion adapted to be received in and guided by the opening 24 of guide 23, that portion of the tool 28 being illustrated by reference numeral 31 in FIG. 4. Further, the end 32 of the tool 28 is adapted to receive a means for effecting rotation of the tool, and for this purpose may have a particularly shaped slot 33 illustrated in FIG. 4. The tool also includes correlating indicia 34—preferably a color code (the color red is indicated by the hatching in FIGS. 3 and 4), and a throughextending opening 35 perpendicular to the interior 30 of the tool 28, for purposes that will be hereinafter described.

A typical rotation-facilitating means for cooperation with end 32 of the tool 28 is illustrated generally by reference numeral 37 in FIGS. 3 and 7. The device 37 comprises a handle having a tubular body portion 38, and a rod 39 passing diametrically through the collar portion 38, and including an interior portion 39' within the collar 38. The collar 38 slips over the end 32 of the tool 28, while the rod portion 39' slips into the slot 33, providing connnection between the handle 37 and tool 28 so that the tool 28 may be rotated by rotating the handle 37.

FIG. 3 illustrates the tool 28 in operative association with the tubular guide 23 and handle 37 in a position wherein it is operative to form a bone plug from the resected femoral head H.

FIG. 3 also illustrates another cutting tool 28', identical to the tool 28 except for color coding and operative dimension, in a storage position in association with the supporting plate 12. The internal diameter 30' of the cutting tool 28' is different from the internal diameter 30 of the cutting tool 28, however the guiding sleeve portion 31 has an external diameter the same as the external diameter of the sleeve 31 of the tool 28. The color coding portion 34' of the tool 28' is different than the color coding 34. In FIG. 3 the color coding portion 34' is hatched to illustrate the color green.

The structure for mounting the tool 28' in storage position—as illustrated in FIG. 3—includes the block 41 which extends downwardly from the bottom surface 14 of the plate 12. The block 41 has a plurality of throughextending bores 42—see FIG. 2—formed therein, one bore 42 for each cutting tool to be held in storage position by the device 10. Each bore 42 is generally parallel to each other bore 42, and the center line thereof is also generally parallel to the bottom surface 14 of the plate 12. The diameter of each of the bores 42 is substantially the same as the diameter of the portion 31 of each of the cutting tools (and thus essentially the same as the diameter of the opening 24 in tubular guide 23). The block 41 has sufficient width so that a substantial portion of each tool 28, 28', etcetera is supported by the block 41 so that the tools will assume the position illustrated for tool 28' in FIG. 3.

In order to hold the tool 28, 28', etcetera in place when held by the block 41, a locking rod 43 (see FIGS. 1 and 2) is provided. The locking rod 43 extends through a bore 44 (see FIG. 3) in the block 41 transverse to the bores 42, and passes through the openings 35 in each of the tools 28, 28'. Any suitable means, such as a detent or screw-threaded portion, may be utilized to hold the locking pin 43 in locking position with respect to the block 41.

Also attached to the plate 12 and extending downwardly from the bottom surface 14 at the end thereof opposite the block 41 is another block 45. The block 45 merely provides a balanced support—with the block 41—for the plate 12 to allow it to rest on a horizontal surface with the rods 18 extending vertically.

According to the present invention there also is provided one, and preferably two or more, elongated rods 50 (see FIGS. 1 and 8 in particular).

Each elongated rod 50 has first—51—and second—52—enlarged generally disc-shaped ends. Each disc end 51, 52 has a predetermined diameter, the diameters of the ends 51, 52 being different than each other. Also, linear distance calibrating indicia, as can be seen by the numerals and lines along the length of the rod 50 in FIG. 8, are provided on each rod 50 at predetermined distances from each of the ends 51, 52 thereof. While indicia in FIG. 8 are only shown for predetermined distances from the end 51, it is to be understood that when the rod 50 is rotated 180° about an axis perpendicular to the disc ends 51, 52, other indicia are provided indicating linear distances from the second end 52.

Each rod 50 also includes correlating indicia, 134, 134', for correlating the diameter of the disc end with which it is associated to the internal diameter of the corresponding tool 28, 28', etcetera. For instance as shown in FIG. 8 the color red is provided as the correlating indicia 134 associated with the end 51, indicating that the diameter (e.g. 18 mm) of the disc 51 is substantially the same as the diameter of the internal passage 30 of the cutting tool 28 having the red correlating indicia 34. Similarly, the color green correlating indicia 134' indicates that the diameter (e.g. 16 mm) of the disc end 52 corresponds to the diameter of the passageway 30' for the cutting tool 28', having the green correlating indicia 34'. In the preferred embodiment it is desirable to provide four cutting tools 28, 28', and two rods 50, so that there are rod ends having diameters of 18 mm, 16 mm, 14 mm, and 12 mm.

The support plate 12 has surface means associated therewith for supporting the rod 50 in a storage position. One rod 50 is illustrated mounted in such a position on the plate 12 in FIGS. 1 and 2, while surface means are provided for mounting another rod in each of those figures, but the rod is not illustrated. Such surface means comprises, for each rod, an elongated linear depression 55 formed in the surface 13 of the plate 12, with enlarged end depressions with through-extending openings 56, and preferably with a central through-extending opening 57. A hold-down component 58 also is provided having a generally horizontally extending surface 59 (see FIG. 2) thereof disposed over the depression 55 and spaced from the bottom of the depression 55 a distance corresponding to the diameter of the rod 50, so as to hold the rod in place. The surface 59 may be pivoted about a vertical axis defined by the screws 60 or the like to move away from the depression 55, to allow the user to place a finger in the cutout 51, grasp the rod 50, and remove it from its storage position.

The support 12 also preferably comprises surface means for mounting the handle 37—or an adapter for attaching the cutting tool 28, 28' to a power drill—in a storage position. This preferably is provided by the bore 62 (see FIG. 1) extending through the plate 12 which receives the collar-shaped body 38 of the handle 37, and a holding component 63—substantially identical to the componnents 58—including a bottom surface 64 thereof (see FIG. 3) which engages the rod 39 of the handle 37.

The support 12 also preferably comprises what can be referred to as notch means for supporting a rod 50 at one end thereof so that it extends upwardly from the surface 13, generally perpendicular thereto, allowing the rod 50 to be used to remove bone plugs from the cutting tool 28, 28'. Such notch means are illustrated generally by reference numeral 66 in FIG. 1, and include a plate portion 67 having a slot 68 therein of essentially the same width as the body of an elongated rod 50, and less than the diameter of any rod end (e.g. 51). The plate 67 is spaced from the surface 13, a sufficient distance to receive a rod end 51, 52, etcetera therebetween.

It is preferred to form all of the components of the device 10 according to the invention of metal. Particularly it is highly desirable for the rods 50 and cutting tools 28, 28', etcetera to be of high grade steel. However in some circumstances some of the components may be made of parts other than metal as long as they are capable of successfully performing their intended functions.

Exemplary apparatus according to the present invention having been described, the method of practicing hip arthroplasty utilizing the apparatus will now be described, with particular reference to FIGS. 3 and 9 through 14.

As a first step in practicing hip arthroplasty, the femoral head H is severed in any conventional manner. Then the interior diameter of the hollow medullary canal 70 of the femur 71 (see FIG. 9) is calibrated. This is accomplished by inserting ends of rods 50 into the canal 70—as illustrated in FIG. 9—until one is found that will fit snugly, but not bind, within the canal 70 at the isthmus. In FIG. 9, the end 51 of rod 50 is illustrated with a snug fit, but not binding, at the femoral canal isthmus, thus it is determined that the diameter of a bone plug to be inserted in the femoral canal should be substantially the same as the diameter of the end 51—e.g. 18 mm.

Simultaneously with the calibrating step described above, the surgeon determines the depth from the femoral neck transection by viewing the distance calibrating indicia (see FIG. 8) on the rod 50. The proposed stem (73) length of the femoral prosthesis 74 is measured against the rod 50, and 2 centimeters is added to the length of stem 73. The rod 50 is thus inserted until one reads indicia thereon corresponding to the length of stem 73 plus 2 centimeters. The indicia readings are taken while the rod 50 is in the position illustrated in FIG. 9.

Once the desired diameter and desired depth for the bone plug have been determined, the surgeon will select the cutting tool having correlating indicia corresponding to the correlating indicia on the selected rod end. For instance with respect to the situation illustrated in the drawings, the cutting tool 28—having the red correlating indicia 34 corresponding to the red correlating indicia 134 of the rod end 51—is selected.

The resected femoral head H is placed between the cup 15 and the movable hold-down component 20 (see FIG. 3), and the nuts 25 are tightened down by rotating the knobs 26 until the head H is firmly clamped between the tubular guide 23 and the cup 15. Then the tool 28 is inserted, cutting end 29 first, into the passageway 24, the portion 31 of the tool 28 being guided by the passageway 24, and the cutting end 29 moving into contact with the head H. Then the handle 37 is placed into operative association with the end 32 of the tool 28, and the surgeon rotates the tool 28, with the handle 37, until a bone plug is cut from the head H. The tool 28, with the bone plug therein, is then removed from the guide 23.

After removal of the tool 28 from the guide 23, it is moved so that it has the orientation illustrated in FIG. 10. The end 52 of rod 50, opposite the selected end 51, is then placed in operative association with the notch means 66 so that the rod 50 extends vertically upwardly from the surface 13, generally perpendicular thereto, with the end 51 on top. The surgeon then places end 32 of the cutting tool 28 over the end 51 of the rod 50, and pushes downwardly. This causes the end 51 to slide within the opening 30 of tool 28, engaging the bone plug P, and ultimately forcing the bone plug out of the tool 28.

Once the bone plug P has been removed from the cutting tool 28 it is cut—if necessary—to the desired length, utilizing a standard bone cutter or osteotome. Then, as illustrated in FIG. 11, it is manually inserted—as with an Adson forceps—into the canal 70. Then, as illustrated in FIG. 12, the rod 50 is placed so that the end 51 thereof contacts the bone plug P, and the rod end 52 is impacted—as with a mallet—to drive the bone plug into the cavity 70 to the predetermined desired depth. This depth is again determined by reading the distance indicia along the length of the rod 50, and tapping of the rod 50 with the mallet is continued until the position of the rod 50 in FIG. 12 is the same as it was in FIG. 9.

Once the bone plug P has been inserted at the desired depth, as illustrated in FIG. 13 a suitable cement 75—such as methylmethacrylate cement is inserted (as by the conventional pressurized technique) into the cavity 70, and the stem 73 of the femoral prosthesis 74 is then inserted into the cavity 70, and held in place by the mement 75. FIG. 14 schematically illustrates the femur 71 with the prosthesis 74 properly in place and the plug P properly serving as a dam for the cement 75.

It will thus be seen that according to the present invention an apparatus has been provided which facilitates the effective formation and positioning of a bone plug of desired diameter, and at desired depth, during hip arthroplasty or the like. The apparatus is extremely simple and easy to use, while being effective, and is useful in practicing the method according to the present invention so that the time and difficulties for performing hip arthroplasty can be substantially reduced.

While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent structures and methods.

What is claimed is:

1. An apparatus for facilitating hip arthroplasty, or the like, comprising:
a rod having first and second enlarged generally disc-shaped ends, each end disc having a predetermined diameter, the first end disc diameter being different than the second end disc diameter; linear calibrating indicia formed on said rod at predetermined distances from each of the ends thereof; and correlating indicia associated with each of said ends, the indicia for the first end distinct from that for the second end; and
first and second hollow bone cutting tools of different effective internal diameter, the first tool having an internal diameter substantially identical to the diameter of the rod first end disc diameter, and said first tool having correlating indicia corresponding to that for the rod first end; said second tool having an effective internal diameter substantially identical to the diameter of the rod second end disc diameter, and having correlating indicia corresponding to that for said rod second end.

2. Apparatus as recited in claim 1 wherein said correlating indicia are colors.

3. Apparatus as recited in claim 1 further comprising x rods, wherein x is an integer greater than or equal to 2, and further comprising 2× cutting tools, each cutting tool having an effective internal diameter substantially identical to the diameter of a rod end disc diameter, and having a correlating indicia corresponding to a correlating indicia for a corresponding rod end, all the rod end disc diameters being different than each other.

4. Apparatus as recited in claim 1 further in combination with means for holding a bone portion and for guiding said cutting tool into operative association with a bone portion held thereby so that a cutting tool may cut a plug from the bone portion held by said holding and guiding means, the bone plug corresponding to the internal diameter of the tool.

5. Apparatus as recited in claim 4 wherein said holding and guiding means comprises a bone portion-receiving cup mounted on a support; a pair of studs extending upwardly from said support generally perpendicular thereto; a movable holding component having defining, apertures therein for receiving said studs, and having a central portion having means defining a tubular guide therein, said tubular guide in alignment with said cup; fixing means for fixing said movable holding component in a particular spaced relationship with respect to said cup to clamp a bone portion between said movable holding component and said cup; said tubular guide having an internal diameter corresponding to a common external diameter portion of each of said cutting tools.

6. Apparatus as recited in claim 4 wherein said holding and guiding means is mounted on a support, and wherein said support includes means for mounting said rod and said tools in a storage position.

7. Apparatus as recited in claim 6 wherein said support further comprises means for receiving either end of said rod and for supporting said rod at said received end so that said rod extends in a position generally perpendicular to said support, held in said generally perpendicular position.

8. Apparatus as recited in claim 6 further comprising rotating means connectable to an end of each of said cutting tools for effecting turning of each of said cutting tools when received by said holding and guiding means; said support including surface means for receipt of said rotating means for mounting it in a storage position.

9. Apparatus as recited in claim 6 wherein said support includes a plate having a first surface, said holding and guiding means upstanding from said first surface; and wherein said support further comprises a block attached to and extending generally perpendicular to a second surface of said plate, opposite said first surface; and wherein said means for mounting said tools in storage positions comprise means defining spaced elongated bores in said block, said bores being substantially parallel to each other and extending in a dimension generally parallel to said plate second surface; means defining a through-extending opening in each of said cutting tools in a portion thereof received by said bore, each said opening extending generally perpendicular to the direction of elongation of said cutting tool; each said bore having an internal diameter corresponding to the external diameter of a portion of said cutting tool containing said through-extending opening; and a locking pin extending through said block and each of said openings, and locking said tools to said block.

10. Apparatus as recited in claim 9 wherein said surface means for mounting said rod in storage position comprises an elongated depression formed in said plate first surface, and in each end of said depression a disc-shaped enlarged depression; said elongated depression having a length corresponding to the length of said rod, and said enlarged depression being dimensioned to receive said disc-shaped ends of said rod; and a releaseable clamping component mounted on said plate first surface and releasably extending over said elongated depression and spaced from the bottom of said depression a distance corresponding to the diameter of said rod, to releasably hold said rod in said depression on said plate first surface.

11. Apparatus facilitating the cutting of bone plugs from bone portions, such as from a femoral head, comprising:
 a support stationarily mounting a cup for receipt of a bone portion, and having a pair of studs upstanding from, and straddling, said cup; a movable holding component including means defining openings therein for receipt of said studs so that said movable component is movable toward and away from said cup guided by said studs; affixing means for affixing said movable component to said studs within a predetermined range of positions to thereby clamp a bone portion between said cup and said movable component; a tubular guide disposed in operative association with said movable holding component, and having an interior diameter aligned with said cup when said movable component is held in operative as sociation with respect to said cup, receiving said studs;
 a plurality of differently dimensioned bone cutting tools, each bone cutting tool having an external diameter guide portion corresponding to the internal diameter of said tubular guide, and each cutting tool having a different internal diameter, corresponding to the diameter of a bone plug to be formed thereby; and
 said support including surface means for mounting each of said tools in a storage position with respect thereto.

12. Apparatus as recited in claim 11 wherein said support includes a plate having a first surface, said holding and guiding means upstanding from said first surface; and wherein said support further comprises a block attached to and extending generally perpendicular to a second surface of said plate, opposite said first surface; and wherein said means for mounting said tools in storage positions comprise means defining spaced elongated bores in said block, said bores being substantially parallel to each other and extending in a dimension generally parallel to said plate second surface; means defining a through-extending opening in each of said cutting tools in a portion thereof received by said bore, each said opening extending generally perpendicular to the direction of elongation of said cutting tool; each said bore having an internal diameter corresponding to the external diameter of a portion of said cutting tool containing said through-extending opening; and a locking pin extending through said block and each of said openings, and locking said tool to said block.

13. Apparatus as recited in claim 11 further comprising rotating means cconnectable to an end of each of said cutting tools for effecting turning of each of said cutting tools when received by said holding and guiding means; said support including surface means for receipt of said rotating means for mounting it in a storage position.

14. Apparatus as recited in claim 11 wherein each of said cutting tools is hollow, having a said predetermined internal diameter; and further comprising a plurality of rods each having an enlarged generally disc-shaped end, the diameter of said disc-shaped end being substantially identical to the interior diameter of a cutting tool; a rod enlarged end corresponding to each of said differently dimensioned cutting tools.

15. Apparatus as recited in claim 14 wherein each rod has first and second of said enlarged generally disc-shaped ends, the diameters of the end discs of each rod being different than each other; and wherein said support further comprises means for receiving either end of said rod and for supporting said rod at said received end so that said rod extends in a position generally perpendicular to said support and held in said generally perpendicular position.

16. Apparatus as recited in claim 15 wherein said support further comprises surface means for receiving said rods for mounting said rods in a storage position.

17. A method of practicing hip arthroplasty, utilizing one or more calibrated rods having enlarged disc-shaped ends of predetermined diameters with correlating indicia associated with each rod end corresponding to the diameter of the rod end, and cutting tools having different internal diameters, the internal diameters of the cutting tools corresponding to the different diameters of the rod ends, and each cutting tool having correlating indicia corresponding to the internal diameter thereof and to the correlating indicia of the corresponding rod disc end diameter; said method including the steps of:
 (a) severing the femur head from the femur of the hip undergoing arthroplasty;
 (b) calibrating the internal diameter of the femur hollow medullary canal by inserting rod ends until a rod end is found having a disc diameter that fits snugly, but does not bind, within the medullary canal approximately at the isthmus;
 (c) simultaneously with step (b), when inserting the rod having the desired disc end diameter, determining the depth from the level of the femoral neck transection including by reading length calibrating indicia on the rod;
 (d) selecting the cutting tool having correlating indicia corresponding to the correlating indicia of the selected rod disc end;
 (e) utilizing the selected cutting tool, forming a bone plug from the resected femoral head;
 (f) cutting the bone plug, if necessary, to the desired length;
 (g) inserting the bone plug into the femoral medullary canal;
 (h) utilizing the selected rod, with the selected rod end in contact with the bone plug, impacting the rod to drive the bone plug to the desired depth, as determined by reading the length calibrating indicia on the rod;
 (i) inserting a suitable cement into the femoral medullary canal; and
 (j) disposing a prosthesis in operative association with the femoral medullary canal so that the prosthesis is held in the appropriate position by the cement.

18. A method as recited in claim 17 comprising the further step (k) of, between steps (e) and (f), removing the bone plug from the cutting tool by forcing the selected rod disc end into the hollow cutting tool to contact the bone plug and move it out of the cutting tool.

19. A method as recited in claim 18 where said step (k) is practiced utilizing a support surface having a notch for receipt of a rod, and is accomplished by inserting the rod end opposite the selected disc end diameter into operative association with the notch so that the rod may extend generally vertically upwardly from the support; moving the hollow cutting tool, with bone plug therein, over the selected end of the rod; and forcing the cutting tool down over the rod so that the selected disc end engages the bone plug and effects relative movement between the bone plug and the cutting tool, expelling the bone plug from the tool.

* * * * *